United States Patent [19]

Sarvazyan

[11] Patent Number: 5,678,565
[45] Date of Patent: *Oct. 21, 1997

[54] ULTRASONIC ELASTICITY IMAGING METHOD AND DEVICE

[75] Inventor: Armen Paruir Sarvazyan, East Brunswick, N.J.

[73] Assignee: Artann Corporation, East Brunswick, N.J.

[*] Notice: The term of this patent shall not extend beyond the expiration date of Pat. No. 5,524,636.

[21] Appl. No.: 607,639

[22] Filed: Feb. 27, 1996

Related U.S. Application Data

[63] Continuation-in-part of Ser. No. 994,109, Dec. 21, 1992, Pat. No. 5,524,636.

[51] Int. Cl.$^6$ .................................................. A61B 8/12
[52] U.S. Cl. ................... 128/774; 128/660.001; 73/787
[58] Field of Search .................. 128/774, 660.01, 128/660.02, 660.06, 660.07, 660.08, 661.03; 73/788, 789, 790, 794–6, 798, 573

[56] References Cited

U.S. PATENT DOCUMENTS

| | | | |
|---|---|---|---|
| 4,250,894 | 2/1981 | Frei et al. | 128/774 |
| 4,423,738 | 1/1984 | Newgard | 128/672 |
| 4,799,491 | 1/1989 | Eckerle | 128/672 |
| 4,802,488 | 2/1989 | Eckerle | 128/672 |
| 4,860,761 | 8/1989 | Yamasawa et al. | 128/686 |
| 5,099,848 | 3/1992 | Parker et al. | 128/661.07 |
| 5,107,837 | 4/1992 | Ophir et al. | 128/660.01 |
| 5,115,808 | 5/1992 | Popovic et al. | 128/660.02 |
| 5,293,870 | 3/1994 | Ophir et al. | 128/660.01 |
| 5,474,070 | 12/1995 | Ophir et al. | 128/661.03 |
| 5,495,771 | 3/1996 | Sumi et al. | 73/789 |
| 5,524,636 | 6/1996 | Sarvazyan et al. | 128/774 |
| 5,557,048 | 9/1996 | Koike et al. | 73/794 |

OTHER PUBLICATIONS

C.R. Gentle, *Mammobarography: a possible method of mass breast screening* (1988) J. Biomed. Eng., vol. 10, pp. 124–126.

R.M. Lerner et al., *Sono–Elasticity: Medical Elasticity Images Derived From Ultrasound Signals in Mechanically Vibrated Targets* (1988) Acoustical Imaging, vol. 16, p. 317.

T.A. Krouskop et al., *A Pulsed Doppler Ultrasonic System for Making Non–Invasive Measurement of Mechanical Properties of Soft Tissue* (1987) 24 J. Rehab. Res. Dev., vol. 24, p. 1.

Ophir et al., *Elastography: A Quantative Method for Imaging the Elasticity of Biological Tissues* (1991), Ultrasonic Imaging, vol. 13, p. 111.

A.P. Sarvazyan et al., *Biophysical Bases of Elasticity Imaging* (1995) Acoustical Imaging, vol. 21, pp. 223–240.

Y. Yamakoshi et al., *Ultrasonic Imaging of Internal Vibration of Soft Tissue Under Forced Vibration* (1990), IEEE Transactions on Ultrasonics, Ferroelectric, and Frequency Control, vol. 7(2), p. 45.

*Primary Examiner*—Robert Nasser
*Attorney, Agent, or Firm*—Mathews, Collins, Shepherd & Gould

[57] ABSTRACT

A method and a device for noninvasively identifying a region of the tissue having a different elasticity than the surrounding tissue by simultaneously measuring strain and stress patterns in the tissue portion using an ultrasonic imaging system combined with a pressure sensing array. In a particular embodiment, a pressure sensing array made of a sound transparent film inserted between the ultrasonic scanner probe and the tissue measures pressure pattern on the surface of the tissue when the tissue portion is deformed while the scanner detects internal strain pattern. The ultrasonic scanner probe with the attached pressure sensing array serves as a pressure exerting member causing a deformation of the tissue and creating stress and strain in the tissue portion.

6 Claims, 8 Drawing Sheets

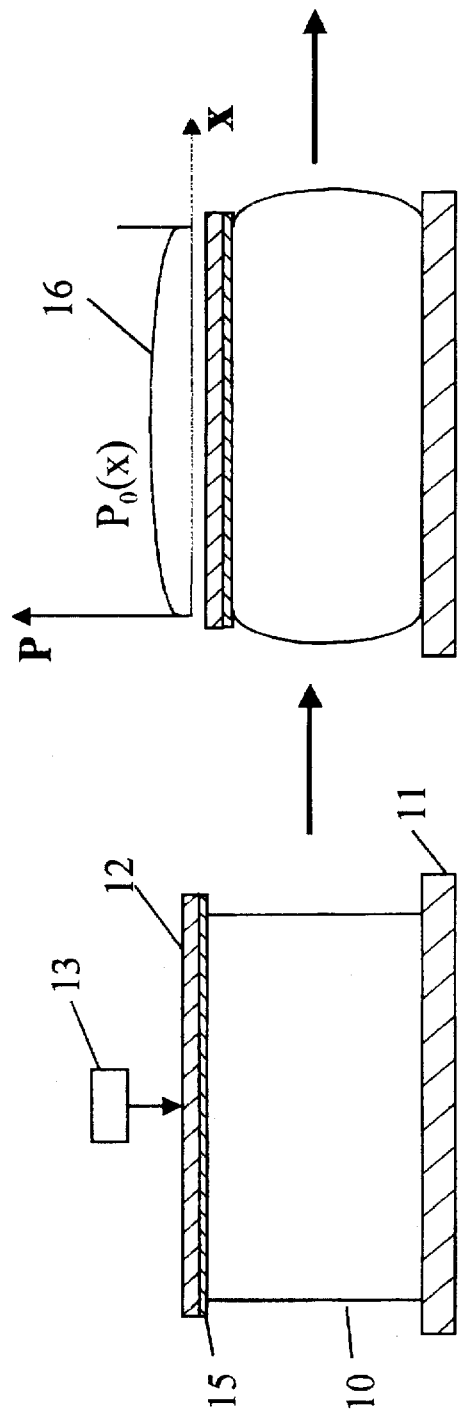
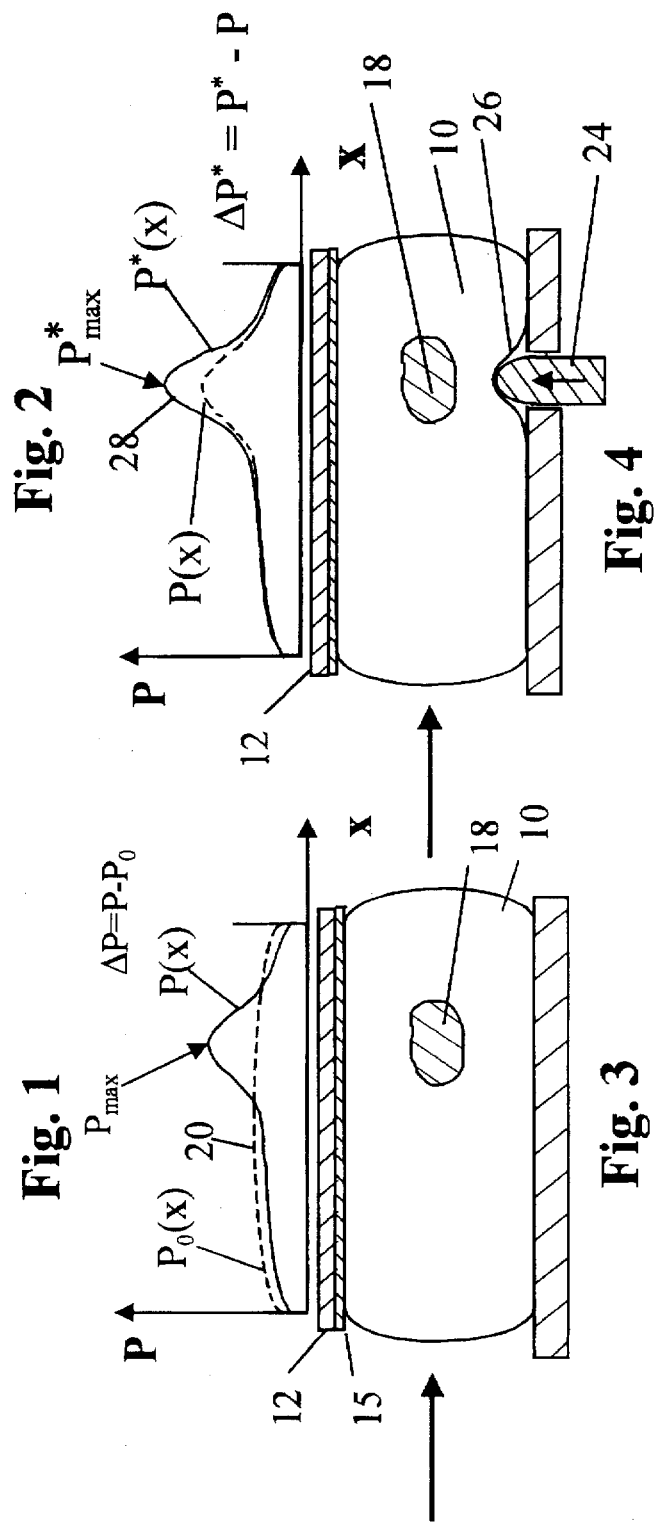
Fig. 1
Fig. 2
Fig. 3
Fig. 4

ULTRASONIC ELASTICITY IMAGING METHOD AND DEVICE

CROSS REFERENCE TO RELATED APPLICATION

This application is a continuation-in-part of U.S. Pat. application Ser. No. 07/994,109, filed Dec. 21, 1992, now U.S. Pat. No. 5,524,636 the full disclosure of which is hereby incorporated by reference herein.

BACKGROUND OF THE INVENTION

1. Technical Field

The present invention relates to a method and a device for determining tissue elasticity in various parts of the body and using such information as a diagnostic tool in the detection of abnormalities of tissue, such as those caused by cancer or other lesions, because the elastic properties of tumors can be significantly different from that of the surrounding tissue.

2. Description of the Prior Art

Diagnosing early formation of tumors, particularly those caused by cancer, has been a problem that has been attempted to be solved using various techniques, such as ultrasonic imaging, nuclear magnetic resonance imaging, x-rays, and the like.

One of the safest and oldest techniques of detecting diseased tissue is palpation (digital examination). Palpation, that is, examination using the sense of touch, is based on the significant differences in elasticity of normal tissues and certain lesions. Palpation has been a commonly used technique for detecting prostate and breast cancer. Several authors have proposed various types of devices mimicking palpation to detect tumors using different types of pressure sensors. For example, Frei et al., U.S. Pat. No. 4,250,894, have proposed an instrument for breast examination that uses a plurality of spaced piezoelectric strips which are pressed into the body being examined by a pressure member which applies a given periodic or steady stress to the tissue beneath the strips.

A different principle for evaluating the pattern of pressure distribution over a compressed breast was proposed by Gentle (Gentle CR, *Mammobarography:—a possible method of mass breast screening*, J. Biomed. Eng. 10, 124–126, 1988). The pressure distribution is monitored optically by using the principle of frustrated total internal reflection to generate a brightness distribution. Using this technique, referred to as "mammobarography," simulated lumps in breast prostheses have been detected down to a diameter of 6 mm. According to Gentle, this technique can be used for mass breast screening; however, no quantitative data on lumps in a real breast was ever published. The failure has been explained by the insufficient sensitivity of the registration system. It should be noted, that most of the development of pressure sensors for medical applications has been done not for mimicking palpation but for monitoring blood pressure and analyzing propagation of pulse waves in blood vessels (See, for example, U.S. Pat. Nos. 4,423,738; 4,799,491; 4,802,488; 4,860,761).

Another approach to evaluate elasticity of the tissues uses indirect means, such as conventional imaging modalities (ultrasound or MRI) which are capable of detecting motion of a tissue subjected to an external force. One approach attempts to determine the relative stiffness or elasticity of tissue by applying ultrasound imaging techniques while vibrating the tissue at low frequencies. See, e.g., K. J. Parker et al, U.S. Pat. No. 5,099,848; R. M. Lerner et al., *Sono-Elasticity: Medical Elasticity Images Derived From Ultrasound Signals in Mechanically Vibrated Targets*, Acoustical Imaging, Vol. 16, 317 (1988); T. A. Krouskop et al., *A Pulsed Doppler Ultrasonic System for Making Non-Invasive Measurement of Mechanical Properties of Soft Tissue*, 24 J. Rehab. Res. Der. Vol. 24, 1 (1987); Y. Yamakoshi et al., *Ultrasonic Imaging of Internal Vibration of Soft Tissue Under Forced Vibration*, IEEE Transactions on Ultrasonics, Ferroelectrics, and Frequency Control, Vol. 7, No. 2, Page 45 (1990).

Another method proposed for measuring and imaging tissue elasticity is described in Ophir et al., U.S. Pat. Nos. 5,107,837, 5,293,870, 5,143,070 and 5,178,147. This method includes emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves is sent along the path into the tissue. The second echo sequence resulting from the second ultrasonic wave pulse is detected and then the differential displacement of selected echo segments of the fast and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

This method includes interposing a layer of a material having a known Young's modulus and speed of sound between a transducer and the tissue to obtain a strain profile of the compressed tissue. The known layer may consist of compressible or compliant material such as rubber, sponge, gels, etc. to provide for an ultrasonic transmission path to the tissue. The change in the time shift between the echoes received from the inner and outer surfaces of the layer under compression provide information on the uniaxial deformation and respective stress in the ultrasonic transmission path through this layer. This technique is further described in Ophir et al., *Elastography: A Quantitative Method for Imaging the Elasticity of Biological Tissues*, Ultrasonic Imaging 13, 111 (1991). The use of this layer is a step forward in the ultrasonic methods of elasticity imaging because it facilitates estimation of tissue elasticity by adding to the measured data on strain profile also a complementary information on the stress in the part of the compressed system. There are two shortcomings to this method. First, to be able to evaluate the stress with sufficient accuracy, the layer must be thick enough to provide measurable time shift between the echoes received from the two surfaces of the layer. This inevitably results in the losses of ultrasonic energy and distortion of the ultrasonic beam. Secondly, the value of the uniaxial stress is adequate only for calculating stress/strain relationships in a one-dimensional system made of infinite parallel layers. The stress in a real system with 3-dimensional inclusions is of a complex character; therefore, a single value of the normal component of stress, such as that obtained in the described method, is a very deficient description of the mechanical state of the system.

OBJECTS AND SUMMARY OF THE INVENTION

The evaluation of mechanical structure of an object requires knowledge of spatial distribution of both stress and strain. Thus, it is a principal object of this invention to overcome the shortcomings of the prior art techniques which merely utilize strain data while stress pattern data is obtained from theoretical assumptions, rather than from the measured data. Still another object of the present invention is to utilize strain and stress data obtained simultaneously for the same region of the object under the same loading conditions and, consequently, to evaluate the mechanical structure of an investigated tissue with less ambiguity. A further object of the present invention is to provide improved method and means for detecting small inclusions, e.g. below 5 mm in diameter, in human/animal tissue. These and other objects and advantages will become evident from the description and drawings which follow.

In sum, the present invention relates to a method and an apparatus for noninvasively identifying a region of the tissue having a different elasticity than the surrounding tissue. The method and apparatus include causing a mechanical deformation of a tissue portion and simultaneously determining patterns of the properties of stress and strain in the deformed tissue portion to determine the presence and location of the differing elasticity regions of tissue.

In a broad sense, the present invention comprises an ultrasonic imaging system combined with a pressure sensing array for investigating tissue elasticity changes, which may indicate tumors. In a particular embodiment, an ultrasonic scanner can be used for detecting the changes in the backscattered signals from the investigated tissue under different loading conditions to obtain the internal strain profiles. A pressure sensing array made of sound transparent film is inserted between the scanner probe and the tissue and can be used for measuring changes in the pressure pattern when the tissue portion is deformed. The pressure sensing array is attached to the probe of the scanner in a preferred embodiment. It has to be assured that the pressure sensing array between the scanner probe and the tissue will not interfere with the scanner operation. The ultrasonic scanner probe with the attached pressure sensing array serves as a pressure exerting member causing a deformation of the tissue and creating stress and strain in the tissue portion.

The method of the present invention includes determining a mechanical model of the investigated tissue portion and iteratively adjusting spatial distribution of elasticity modulus in the tissue portion until the mechanical properties of the model will match with the measured patterns of stress and strain.

Before referring specifically to the drawings, and without being bound by any particular posited theory, the theoretical aspects of the invention are discussed. Pressure pattern on the surface of an investigated tissue portion together with given boundary conditions enable one to reconstruct internal structures in underlying tissue and to evaluate relative hardness and softness of tissue in localized areas. The present invention utilizes the relationship between elasticity differences in localized areas inside of tissue, the stress pattern on the surface of the tissue, and internal strain pattern. This relationship forms the theoretical basis for a method of detecting and quantifying tissue abnormalities.

When calculating the mechanical properties of tissues, calculations are based on a model of the tissue as being linearly elastic and incompressible media. Such an approach is a first approximation which is sufficient to solve all questions arising in mechanical elasticity imaging.

Accordingly, the graphical representations discussed in the detailed description of the invention are based on calculations from the general equations presented below. The following equations are general equations for three dimensional linear theory of elasticity for in-compressible media like tissues or another water based system, that is a system having a Poisson's ratio of 0.5 (Sarvazyan et al., *Biophysical Bases of Elasticity Imaging*, Acoustical Imaging, Vol. 21, 223, 1995).

The equations for dynamic equilibrium are:

$$\frac{\partial \sigma_{xx}}{\partial x} + \frac{\partial \sigma_{xy}}{\partial y} + \frac{\partial \sigma_{xz}}{\partial z} = \rho \frac{\partial^2 U}{\partial t^2} \quad (1)$$

$$\frac{\partial \sigma_{xy}}{\partial x} + \frac{\partial \sigma_{yy}}{\partial y} + \frac{\partial \sigma_{yz}}{\partial z} = \rho \frac{\partial^2 V}{\partial t^2}$$

$$\frac{\partial \sigma_{xz}}{\partial x} + \frac{\partial \sigma_{yz}}{\partial y} + \frac{\partial \sigma_{zz}}{\partial z} = \rho \frac{\partial^2 W}{\partial t^2}$$

Where:

U, V, W are components of displacement;

$\rho$ is density of media; and $\sigma_{ij}$ are components of stress tensor.

The pattern of stresses must be related to a pattern of strain. This relationship for incompressible media (e.g. tissues or other water based systems) is given by the following equations:

$$\sigma_{xx} = P + 2\mu E_{xx} \quad \sigma_{yy} = P + 2\mu E_{yy} \quad \sigma_{zz} = P + 2\mu E_{zz} \quad (2)$$
$$\sigma_{xy} = 2\mu E_{xy} \quad \sigma_{xz} = 2\mu E_{xz}, \quad \sigma_{yz} = 2\mu E_{yz}$$

where $$\mu = \frac{E}{2(1+\nu)}, \nu = 0.5 \text{ is Poisson's ratio, } E \text{ is Young's Modulus, and}$$

$$E_{xx} = \frac{\partial U}{\partial x} \quad E_{yy} = \frac{\partial V}{\partial y} \quad E_{zz} = \frac{\partial W}{\partial z}$$

$$E_{xy} = \frac{1}{2} \left( \frac{\partial U}{\partial y} + \frac{\partial V}{\partial x} \right) \quad E_{xz} = \frac{1}{2} \left( \frac{\partial U}{\partial x} + \frac{\partial W}{\partial z} \right)$$

$$E_{yz} = \frac{1}{2} \left( \frac{\partial V}{\partial z} + \frac{\partial W}{\partial y} \right)$$

By combining equations (1) and (2), we can obtain three equations containing only three unknowns, U, V, W, which are components of displacement plus the unknown pressure P.

An additional equation is the equation of incompressibility showing that divergence of vector of displacement equals zero:

$$\frac{\partial U}{\partial x} + \frac{\partial V}{\partial y} + \frac{\partial W}{\partial z} = E_{xx} + E_{yy} + E_{zz} = 0$$

This last equation represents the condition that when force is applied to the soft tissue, all the deformation of tissue is related to changes of the shape of the soft tissue but not the volume, because Poison's ratio is 0.5, that is the bulk compressional modulus of soft biological tissues is many orders of magnitude higher then the shear elasticity modulus (Sarvazyan et al., *Biophysical Bases of Elasticity Imaging*, Acoustical Imaging, Vol. 21, 223, 1995).

The mechanical characteristics of tissue involve not only elasticity as discussed, but also viscosity. Thus, the tissue is a viscoelastic material that requires description in both viscous and elastic components. Viscosity affects the information received because with a viscoelastic material, there is a time delay between force application and any displacement that occurs. In a dynamic mode where force is applied in time, the development of stresses in time provides the information on viscosity.

In case of viscoelastic media, the components of the stress tensor in equation (2) should have following additional terms for shear viscosity, $\mu^*$ $$2\mu^* \frac{\partial E_{ij}}{\partial t}$$

The shear modulus and Young's modulus of soft tissue are different by a factor of 3, because Poisson's ratio is 0.5. While either modulus can be used for examination of the tissue, Young's modulus is used in the description of the present invention.

In the case of harmonic disturbances, temporal dependence can be easily removed from these equations and the system of the differential equations for amplitudes will be obtained.

With the foregoing and other objects, advantages and features of the invention that will become hereinafter apparent, the nature of the invention may be more clearly understood by reference to the following detailed description of the invention, the appended claims and the several views illustrated in the drawings.

BRIEF DESCRIPTION OF THE DRAWINGS

FIG. 1 is a schematic representation of a model of soft "tissue" illustrating a device for loading incorporating pressure sensors used in the present invention;

FIG. 2 is the device of FIG. 1 after loading the tissue, and illustrating a typical pressure curve across a surface of the tissue;

FIG. 3 is similar to the tissue compression in FIG. 2, with the effect of a presence of a tumor in the tissue illustrated;

FIG. 4 is an illustration of the structure shown in FIG. 3, with a piston deforming tissue from a side opposite from the pressure plate;

DETAILED DESCRIPTION OF THE PREFERRED EMBODIMENTS

Figure 5:
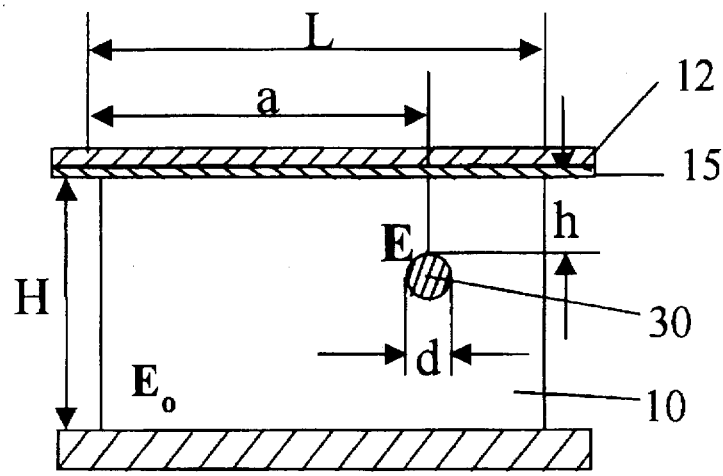
FIG. 5 is a schematic illustration of loading parameters for a model tissue being examined and a tumor in such tissue.

Referring now to the drawings, like elements are designated by like numerals. FIG. 1 illustrates a portion of a soft tissue 10 that is supported on a base 11 and which supports a flat rigid plate 12 capable of exerting pressure thereon from a force generator 13. A series of individual pressure sensors indicated at 15 are provided on the bottom surface of the plate 12 to sense pressure in an array across the surface of the soft tissue 10.

FIG. 2 represents a pressure profile P(x) of the homogenous tissue 10 when deformed. FIG. 3 illustrates a homogeneous tissue pressure profile in the dotted line and in the solid line the pressure profile for tissue 10 having an inclusion 18. The difference between these two pressure profiles shown in FIG. 3 provides information on the presence, location, and relative elasticity of inclusion 18 in respect to surrounding tissue 10. The strain pattern on the surface of the tissue 10 as shown in FIG. 3 is in this case represented in the form of pressure profile P(x). This strain pattern depends on the presence of an inclusion 18, as well as on the dimension of the tissue portion, neighboring anatomical features of that tissue, such as presence of a bone, and on the geometrical relationship of the tissue 10, base 11 and deformation member 12. Therefore, not the strain profile P(x) itself, but the difference between the measured profile P(x) and the profile $P_o(x)$, shown by the dotted line, theoretically calculated for a homogenous model of that tissue under same boundary conditions, provides direct information on the inclusion.

FIG. 4 schematically illustrates how the present invention enhances the amplitude of the pressure profile and, thus, improves detection of an inclusion. In this instance, the tissue 10 is supported on a base 11, and a schematically shown piston or block 24 which also is called a "finger" as used in palpation, is provided on base 11 and is caused to protrude into the tissue and compress the tissue in a localized area indicated at 26 directly below the inclusion 18, which can be a tumor.

The represented pressure profile schematically disposed on the top of the pressure plate 12 (which is displaced the same as that previously explained) represents the data provided by the pressure sensors 15. P(x) is represented as a dashed line and is the profile substantially as that shown in FIG. 3. P*(x), indicated by line 28, represents the pressure profile resulting from the presence of the piston 24 directly under the tumor. The piston 24 acts like a probe to cause extra compression in the desired region (e.g., inclusion 18) in addition to the general compression of the tissue block 10 between plate 12 and base 11. This results in a substantial increase in the pressure profile P*(x) which reaches a maximum at $P^*_{max}$ directly over the tumor. By comparing the respective pressure profiles P(x) and P*(x), one can recognize that a much greater amplitude of the pressure profile can be obtained from the pressure sensors (to indicate an abnormality) when a probe (e.g., piston 24) or other extra compressive force is directed in the region of a tumor. In this case, a change in the pressure profile amplitude because of the piston 24 is represented as $\Delta P^* = P^* - P$.

FIGS. 5–13 are schematic examples to illustrate the applicability of the theory to the methods and devices disclosed, and to show the range of variables and measured parameters available for calculating meaningful values for quantitative analysis and evaluation. The illustrations of tissue are not meant to represent any particular portion of a human body.

Figure 5A:
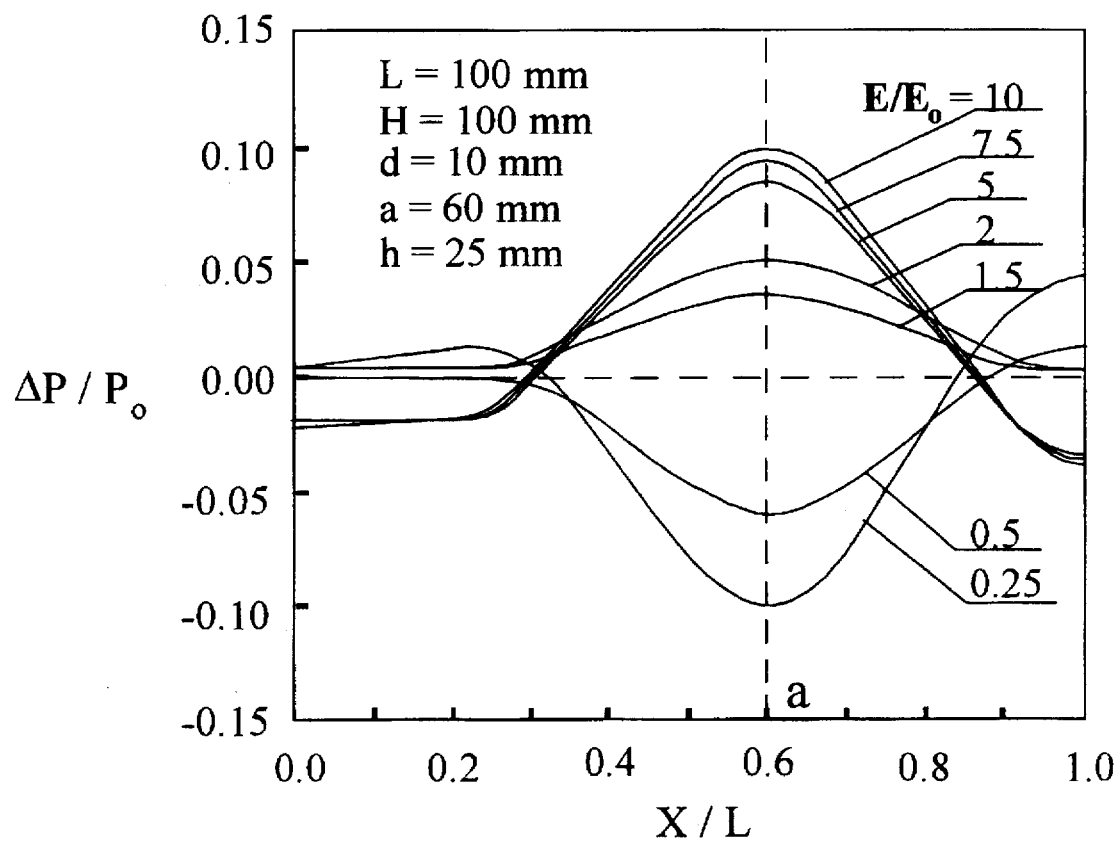
FIG. 5A is a plot of calculated differential pressure ratio across the surface at differing ratios of moduli of elasticity ratio between surrounding tissue and a tumor.

In FIG. 5, a schematic representation illustrates tissue having a tumor therein of a certain size and location. The graph of FIG. 5A illustrates a particular calculated differential pressure ratio as a function of the distance along the horizontal axis on the surface of the tissue. The graph is based on the dimensions shown in FIG. 5 having certain values, such as those listed in FIG. 5A. The symbol (E) represents the elasticity modulus (Young's modulus) of the tumor and ($E_o$) represents the elasticity modulus (Young's modulus) of the surrounding tissue. A ratio of these two moduli of elasticity ($E/E_o$) provides an indication of the hardness of the tumor relative to the surrounding tissue.

It is known that the Young's or shear elasticity modulus of a tumor varies significantly from the modulus of elasticity for surrounding tissue. For example, carcinoma may have an elasticity modulus of 10 times the elasticity modulus of normal tissue. However, in some cases, the elasticity modulus of tumors may not be substantially different from that of normal tissue, making the tumors "nonpalpable". FIGS. 5 and 5A illustrate that the differential pressure profile ratio, namely ($\Delta P/P_o$), (a change in amplitude of the pressure sensed at an inclusion divided by the pressure in that region of normal tissue) in the region surrounding the tumor is quite sensitive to changes in the elasticity modulus ratio ($E/E_o$).

In FIG. 5, a "block" of tissue 10 has a height H from a base to the contact point with the pressure sensors 15, and has a length L extending along the "X" direction (i.e., horizontal axis). A tumor 30 is positioned in the tissue 10, and is located a distance below the loading plate 12 equal to (h) and it has a diameter (d). Tumor 30 is located along the horizontal axis at a distance (a) from a left edge of the tissue 10.

FIG. 5A is a graph illustrating the differential pressure ratio ($\Delta P/P_o$) (values shown on the vertical axis), as a function of the distance along the X axis from the left edge of the tissue 10 to the right. The position of the tumor 30 at (a) is indicated by a vertical dotted line in FIG. 5A. Several plots of ($\Delta P/P_o$) as a function of (X/L) are shown, each corresponding to a given ratio of moduli of elasticity ($E/E_o$), which indicates the relative hardness between a tumor and normal tissue.

With the parameters having the values shown in FIG. 5A, the plots illustrate that a tumor/tissue combination having an elasticity moduli ratio ($E/E_o$) of only 1.5, i.e., the tumor having a modulus of elasticity of 1.5 times that of the surrounding tissue, a detectable change in the pressure signal of about 3% is observed for the region surrounding the tumor. This means that even tumors that are not much harder than surrounding tissue can be detected quite easily. It is known that a tumor in a breast, for example, can be detected by a palpation (which is the only technique available for evaluating elasticity), but palpation is reliable only when the tumor has progressed so its Young's modulus is more than five to ten times larger than that of surrounding tissue. The differential pressure signal ($\Delta P/P_o$) shows a more pronounced effect near the tumor when the elasticity moduli ratio ($E/E_o$) is 2 or 5 or more. However, in this case when the elasticity moduli ratio is greater than 7.5 (e.g., 10), there is not a substantial increase in the differential pressure profile above that shown for $E/E_o$=7.5.

When tumors or inclusions are softer than the surrounding tissue, e.g., the ratio ($E/E_o$) is 0.5, a substantial difference in the differential pressure profile ($\Delta P/P_o$) in the region of the tumor is readily observable. A more pronounced effect occurs when the ratio ($E/E_o$) is 0.25. Accordingly, by observing a relatively small change in the pressure profile (only 2–10%), one can detect tumors that have a relatively small change in the modulus of elasticity. This clinically significant data is obtained by using a pressure sensor array extending across the surface of the tissue and external to the tissue that measures a pressure profile response during compression of the tissue.

Figure 6:
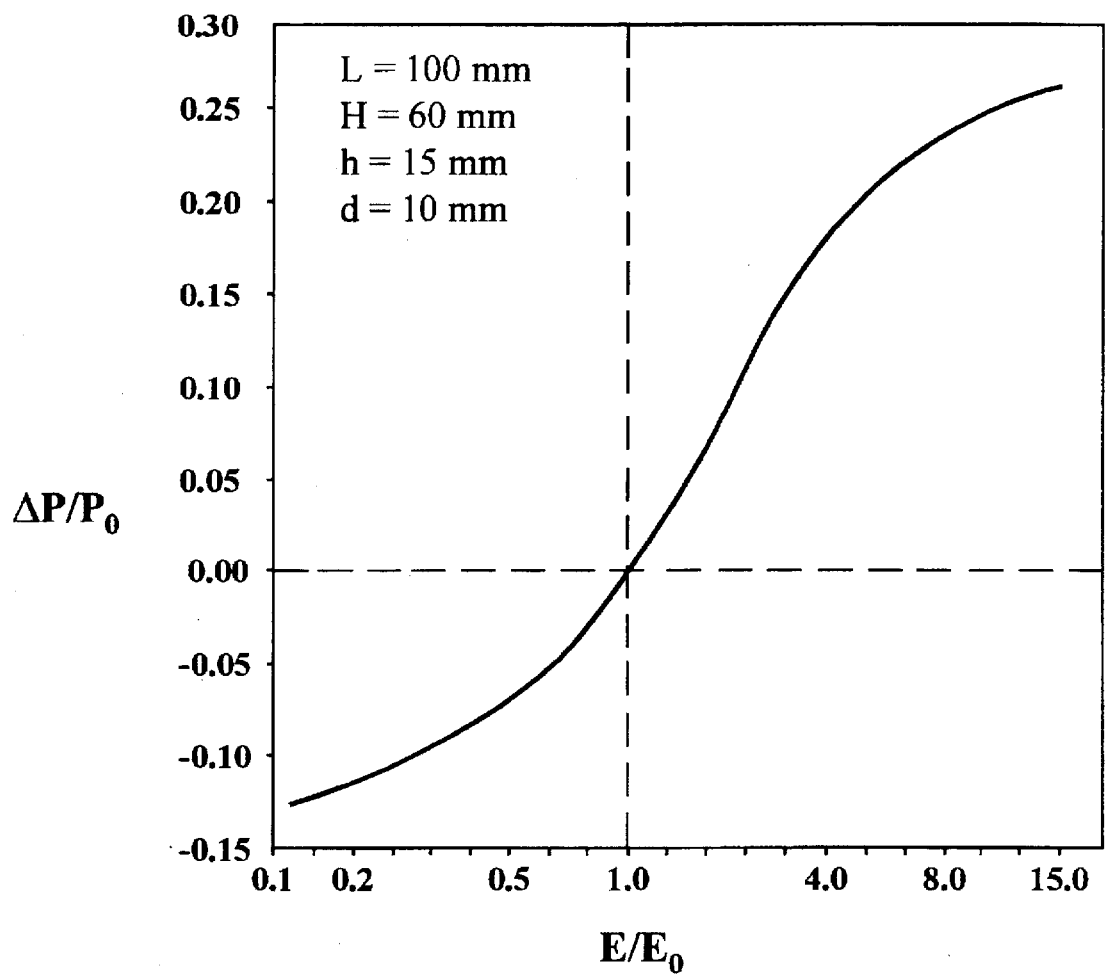
FIG. 6 is a graphical representation of the calculated relationship between differential pressure ratio and moduli of elasticity ratios for a loading structure shown in FIG. 5.

FIG. 6 illustrates the changes in pressure as a function of the change in the elasticity modulus ratio ($E/E_o$).

Similar to the illustration on FIGS. 5 and 5A, FIG. 6 shows that easily achievable resolution of a few percent in the pressure profile ratio ($\Delta P/P_o$) can enable one to detect inclusions differing from the surrounding tissue in hardness to an extent which does not permit palpatory detection. The graph is based on a tissue block 10 having the parameters such as indicated on FIG. 6. The values on the horizontal axis ($E/E_o$) are provided on a logarithmic basis to facilitate comparison purposes.

Figure 7:
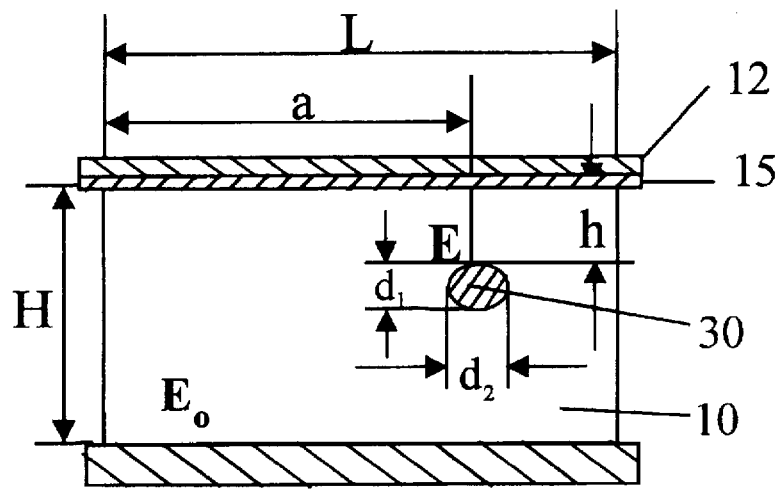
FIG. 7 is a schematic representation similar to that shown in FIG. 5 with certain loading parameters illustrated.
Figure 7A:
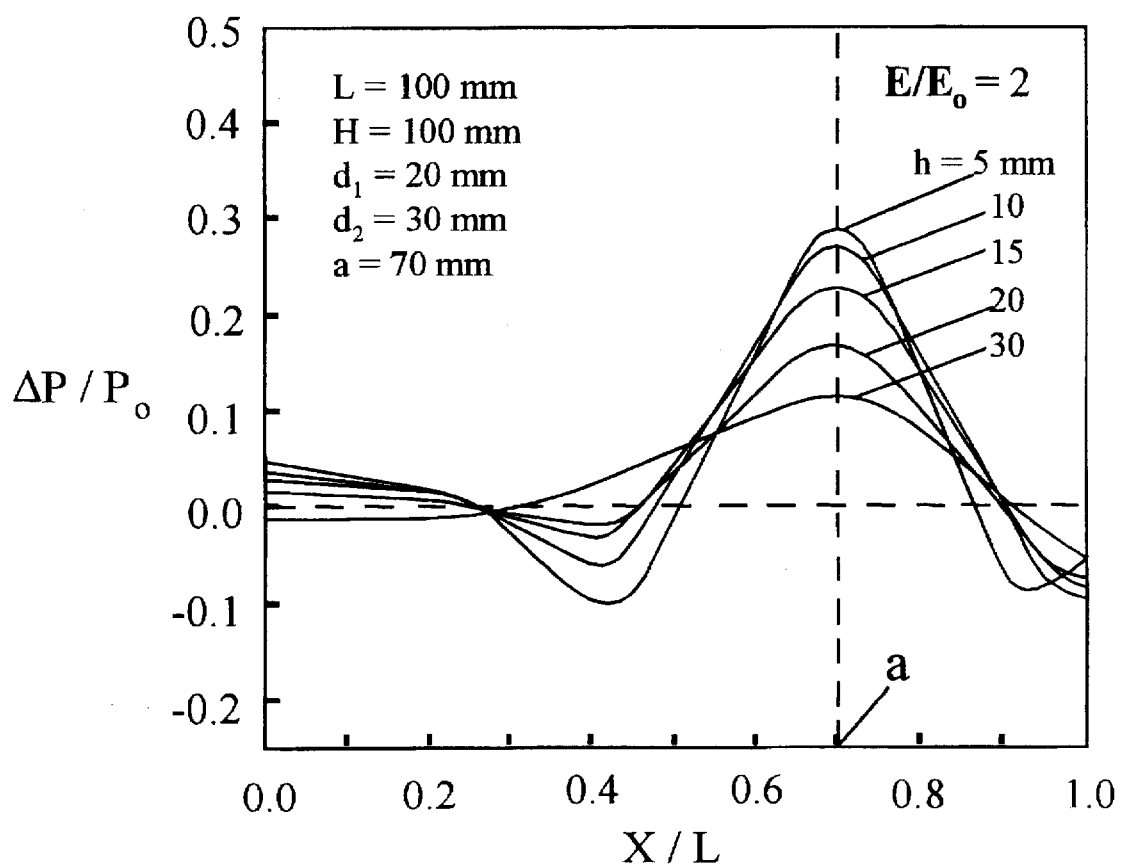
FIG. 7A is a graphical representation of the calculated differential pressure ratio across the surface at differing depths of a tumor in tissue shown at FIG. 7.

FIGS. 7 and 7A illustrate that the capability to detect a tumor within a block of tissue depends on the distance of the tumor from the tissue surface (skin) and pressure sensors. As seen in FIG. 7, the block of tissue 10 has a tumor 30' located therein and, in this instance, the vertical height of the tumor is represented as $d_1$ and the lateral width of tumor is represented as $d_2$. The parameter (a) represents the tumor's distance from its position from the left side of the tissue block. A set of values for the dimensions shown in FIG. 7 are listed on in FIG. 7A. FIG. 7A shows the calculated plot of the pressure profile ratio ($\Delta P/P_o$) (the change in pressure of tumor tissue relative to normal tissue divided by the pressure sensed with no tumor) as a function of (X/L) along the X axis. This graph illustrates that a substantial change in the pressure profile ratio ($\Delta P/P_o$) of about 0.3 is observed when the tumor is a small distance (h=5 or 10 mm) from the tissue surface and that a smaller change in pressure profile ratio occurs when the tumor is far from the surface (e.g., h=30 mm). However, even when the tumor is deep (h=30 mm), the pressure profile ratio change is still readily discernible (with ($\Delta P/P_o$ about 0.1 which is quite measurable) to indicate a tissue abnormality at about X/L=0.70. The ratio of ($E/E_o$) is taken to be equal to 2.

Figure 8:
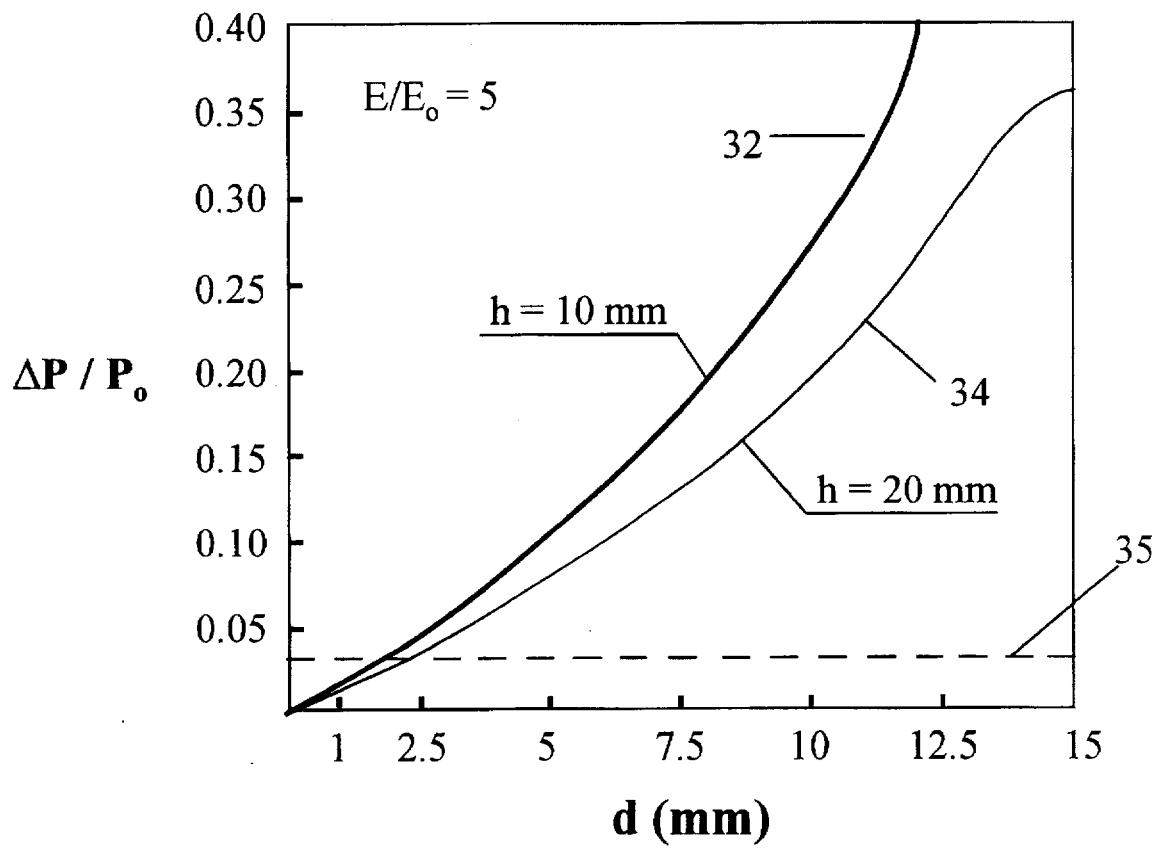
FIG. 8 is a graphical representation of calculated differential pressure ratio relative to the diameter of a tumor being sensed at differing depth of the tumor as shown in FIG. 5.

FIG. 8 illustrates the effect on the ability to ascertain a change in pressure with the sensors 15 as a function of the change in the diameter d of the tumor 30. As seen in FIG. 8, the elasticity moduli ratio ($E/E_o$) is equal to five, and the graph shows a plot of ($\Delta P/P_o$) versus d for a tumor with h=10 mm (indicated by line 32) and a tumor with h=20 mm (indicated by line 34). The pressure ratio ($\Delta P/P_o$) at the point of surface above the tumor, is indicated along the vertical axis, while the diameter of the tumor d is indicated along the horizontal axis.

The reference line indicated as 35 is more or less the base line for sensitivity of the ratio ($\Delta P/P_o$) measurement that can be easily obtained with existing pressure sensors. An accuracy of about three percent for pressure sensors is quite achievable, and the base line 35 represents a change of about three percent, which will give a clear indication of the presence of a tumor in normal tissue having a diameter (d) in the range of one to two millimeters. FIG. 8 indicates that, the larger the tumor, the greater is the change in the pressure ratio.

In the case of breast tumors, palpation typically reveals tumors only larger than 5–10 mm in diameter. Detection of breast tumors with diameters of about 2–3 mm is a crucial point for providing early diagnostics of breast cancer.

Figure 9:
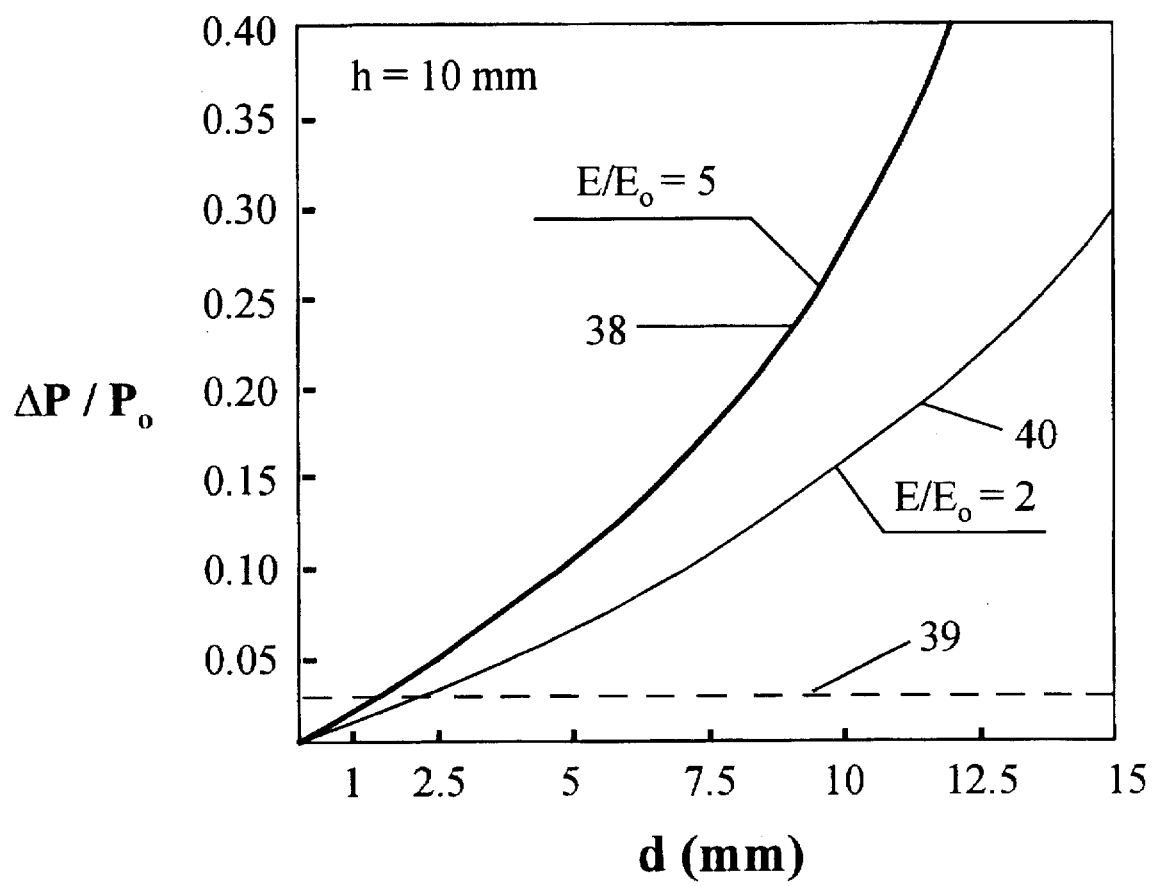
FIG. 9 is a graphical representation of the calculated differential pressure ratio relative to the diameter of a tumor, at differing ratios of moduli of elasticity between the surrounding tissue and the tumor.

FIG. 9 again illustrates the change in the pressure profile ratio ($\Delta P/P_o$) at the point of surface above the tumor as a function of the diameter (d) of the tumor. However, this time, the depth (h) of the tumor below the sensors 15 is set at 10 mm and a plot is provided for the case when the elasticity moduli ratio ($E/E_o$) equals 5 (indicated by upper curve 38) and when ($E/E_o$) equals 2 (indicated by lower curve 40). As expected, the greater the difference in the elasticity modulus between the tumor and surrounding tissue, (a larger ratio ($E/E_o$)), the more substantial change in the pressure profile ratio ($\Delta P/P_o$) for a given diameter tumor and the more easily the tumor will be detected. Taking the ratio ($\Delta P/P_o$) as an indication of sensitivity, one can observe line ($E/E_o=5$) crossing a threshold level of sensitivity (indicated by the dashed line at 39) indicating that detection of a tumor in the range of 1 mm can be made. When an elasticity modulus ratio is 2 (curve 40), one can observe that a tumor of 2.5 mm in diameter (d) could be detected. It is well known that palpation permits detection of tumors only if their diameter is over 8–10 mm, but not smaller. The graph in FIG. 9 shows quantitatively how the detection device (pressure sensors) becomes substantially more sensitive (on a relative basis, i.e., a larger change in the pressure profile ratio ($\Delta P/P_o$) is observed) as the elasticity moduli ratio ($E/E_o$) of the tumor tissue relative to the normal tissue increases.

Combined systems can be utilized including pressure sensors that determine surface conditions, and scanners such as MRI, x-ray or ultrasound scanners which provide information about deformations and corresponding strain profiles of internal structures under various loading conditions. The pressure sensing arrays can indicate stress profiles on the surface and the conventional scanners give information about the changes in geometry of any internal structures and corresponding strain pattern. Thus the calculation of elasticity of internal tissues will be performed with higher resolution and, additionally, regions of interest in the images produced by an imaging device can be characterized in the terms of relative elasticity or hardness. This will increase diagnostic capability of the existing imaging methods in tumor diagnostics.

Figure 10:
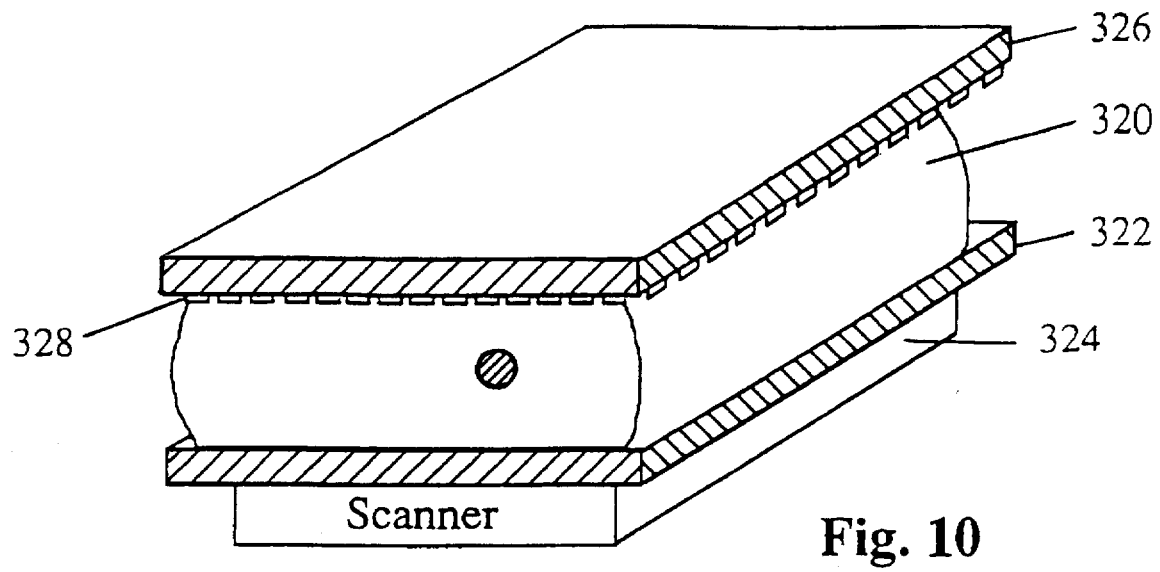
FIG. 10 is a schematic representation of a combined system deformation device in which a pressure sensor array located on top of the tissue and an ultrasonic scanner is located below the tissue on a side opposite from the pressure sensor array.
Figure 11:
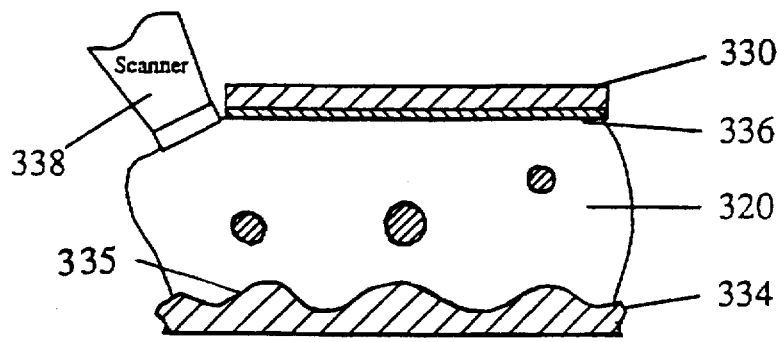
FIG. 11 is a cross-sectional view schematically depicting a pressure sensor array positioned on top of a tissue block with an ultrasonic scanner disposed on a side of the tissue with the tissue supported by an irregular surface.

In FIGS. 10 and 11, a combined system is illustrated. In FIG. 10, a mass of tissue indicated at 320 is supported on a suitable support 322, which has a scanner and associated probe 324 mounted thereon on a bottom side, or from an opposite side from the tissue. The tissue is compressed with a support plate 326 that has a plurality of individual pressure sensors in an array indicated generally at 328. The pressure array at the surface as shown provides a pressure distribution depending on the structure and elasticities of internal tissues.

FIG. 11 is a modification of the device in FIG. 10 and includes a pressure plate 330 acting on tissue 320, which is supported on a support plate 334 in the model shown, which is simulating soft tissue to which access can be provided from one side and on the opposite side supported by skeletal elements, such as the bone structure. In this embodiment, the support plate 334 has an irregular surface 335, representing a bony or skeletal structure underlying investigated soft tissues. This results in a different pressure profile which is measured using the pressure sensors 336 located on the bottom of the plate 330. A scanner and its associate probe 338 is positioned alongside the tissue and angled relative to the tissue, is used for imaging the changes in the internal geometry of the tissue 320 under different loading conditions to obtain the internal strain profiles. Again, the scanner probe can be of any desired form, but by analyzing both the stress pattern on the pressure sensors 336 and the internal strain patterns from the scanner, information about an inclusion in the tissue can be obtained. This information includes the elasticity as well as positional and dimensional information about the inclusion.

Figure 12:
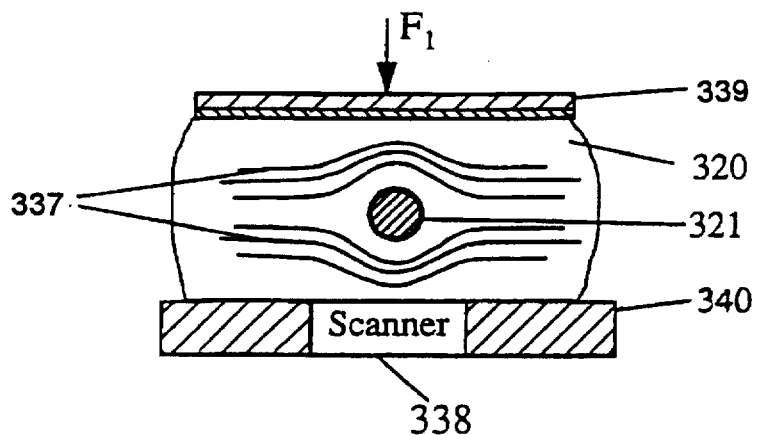
FIG. 12 is a cross-sectional view schematically depicting the strain profiles resulting from compression of a tissue block with a hard tumor therein.

In FIG. 12, a representation of strain pattern or strain profile (shown as lines 337) of a compressed tissue 320 is shown with an inclusion 321 (e.g., cross section of a tumor) therein. Plate 339 is moved in a vertical direction, as indicated by the arrow $F_1$, to compress tissue 320 supported on support 340. The strain profiles 337 of tissue are depicted within tissue 320, and above, below, or in both sides, of the inclusion 321. These strain profiles detected by a scanner 338 depend on the mechanical structure of tissue.

Figure 13:
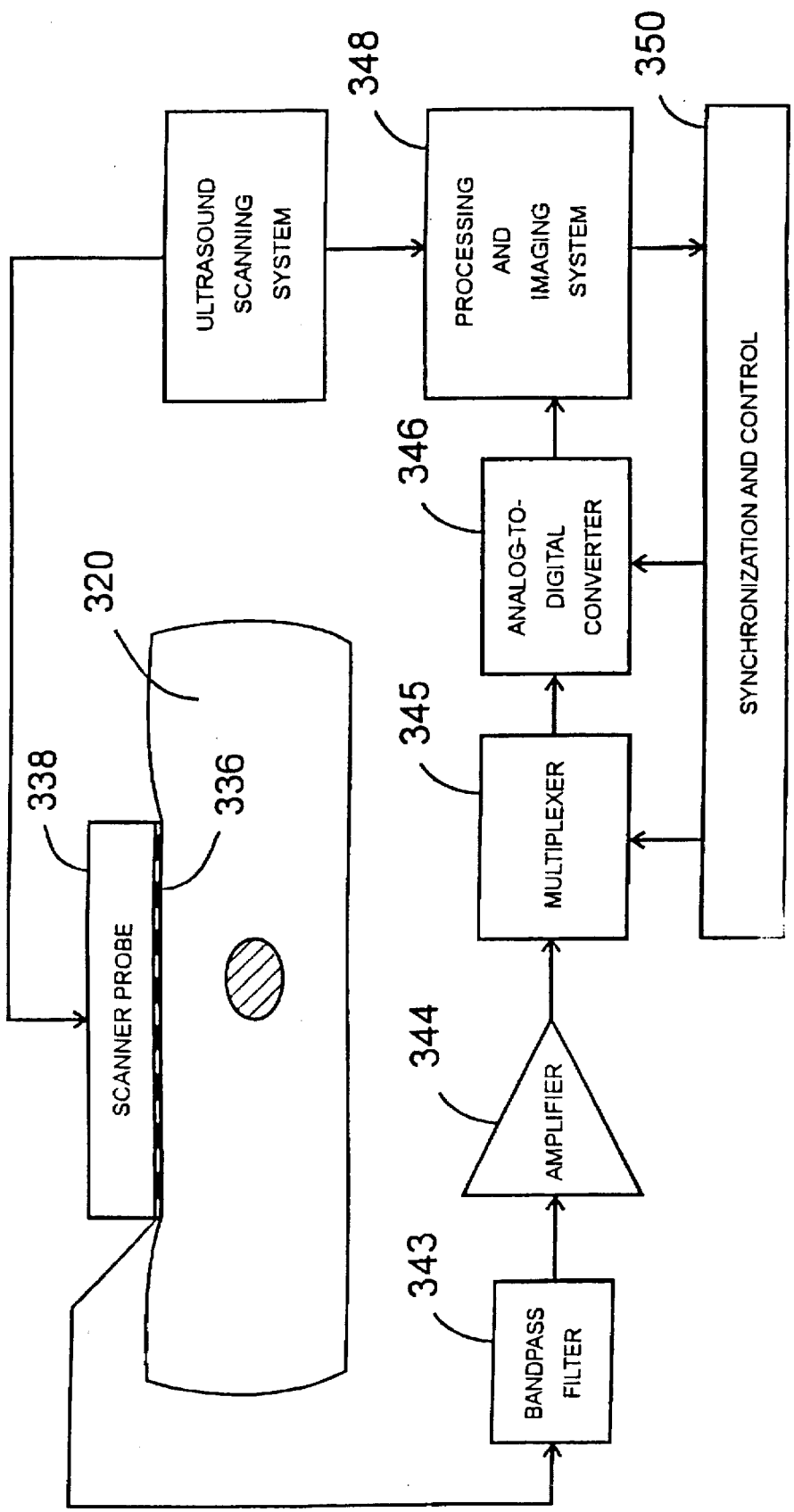
FIG. 13 is a schematic representation of the preferred embodiment in which a pressure sensor array is positioned between a scanner and the tissue to be scanned.

FIG. 13 is a variation of the embodiments of FIGS. 10–12 in which a pressure sensing array 336 is attached to the surface of the scanner probe 338 facing the bodily tissue 320. This embodiment can be used on tissues that are accessible only from one side. The pressure sensing array according to the present invention is made in a form of a sound-transparent film. An example of such a thin film pressure sensing array is Tekscan resistive array (manufactured by Tekscan, Inc. Boston, Mass.). Sound-transparent pressure sensing array can be made also using films of a piezoelectric polymer polyvinylidene fluoride (PVDF) or its copolymers (manufactured by AMP Incorporated, Valley Forge, Pa.).

The pressure sensing array 336 is placed between the scanner probe 338 and the tissue 320. The array 336 may be attached to probe 338 or it may be separate from the probe 338 and held in place by the weight of the probe 338 or the force being applied to the probe 338. Signals from each individual sensor in array 336 are brought to an input buffer amplifier 340 which also includes an input bandpass filter 343. The signals from the array 336 are further multiplexed by multiplexer 344, converted to digital signals in an analog-to-digital converter 346 and analyzed by the processing and imaging system 348. The processing system also controls the synchronization and control circuitry 350.

Although the present invention has been described with reference to preferred embodiments, workers skilled in the art will recognize that changes may be made in form and detail without departing from the spirit and scope of the invention.

What is claimed is:

1. A method of identifying a region within a tissue portion having a different elasticity than the surrounding tissue comprising:

causing a deformation of the tissue and creating stress and strain in the tissue portion by an ultrasonic scanner probe pressed against the tissue portion;

determining both of the properties of the created stress and strain in the tissue portion by measuring pressure distribution using a pressure sensing array to obtain a stress pattern on the surface of the tissue portion and imaging internal tissue structure by said ultrasonic scanner to provide the internal strain pattern after deformation, wherein the pressure sensing array and the ultrasonic scanner probe are located at the same location on the surface of the tissue portion;

defining a model of the tissue portion with homogeneous tissue and with given boundary conditions for the tissue portion;

calculating patterns of the both of the properties of stress and strain for the defined model;

comparing the determined patterns obtained in the determining step and the respective calculated patterns obtained in the calculating step, the differences between the patterns indicating the presence and location of a different elasticity region of tissue within the tissue portion; and evaluating elasticity characteristics of the tissue portion by varying a spatial distribution of modulus of elasticity in the defined model to minimize the difference between the determined patterns from the determining step and the respective calculated patterns for the defined model, thereby solving an inverse mechanical problem and obtaining spatial distribution of elasticity modulus in the tissue portion.

2. A device for determining variations in elasticity of bodily tissue comprising:

means for applying pressure to an accessible surface of said tissue to provide at least two conditions of compression loading of the tissue to be examined, said means comprising an ultrasonic scanner probe;

means for measuring both of the properties of the created stress and strain in the tissue portion, said means comprising a pressure sensing array to provide pressure pattern on the surface of the tissue portion, and an ultrasonic scanner to provide the internal strain pattern in the tissue portion after deformation, wherein the pressure sensing array and the probe of the ultrasonic scanner are adapted to be located at the same location on the surface of the tissue portion; and means for processing the measured data and obtaining spatial distribution of elasticity modulus in the tissue portion.

3. The device of claim 2, wherein said pressure sensing array is made out of a sound transparent film positioned between the tissue and the surface of an ultrasonic scanner probe facing the tissue.

4. The device of claim 3, wherein the pressure sensing array is made out of piezoelectric polymer film.

5. The device of claim 3, wherein the pressure sensing array is a pressure sensitive resistor based array.

6. A method for determining variations in elasticity of bodily tissue comprising the steps:

applying pressure by ultrasonic scanner probe to an accessible surface of said tissue to provide at least two conditions of compression loading of the tissue to be examined;

measuring both of the properties of the created stress and strain in the tissue portion, using a pressure sensing array to provide pressure pattern on the surface of the tissue portion, and an ultrasonic scanner to provide the internal strain data in the tissue portion after deformation; and processing the measured data and obtaining spatial distribution of elasticity modulus in the tissue portion.

* * * * *